(12) United States Patent
Alimi et al.

(10) Patent No.: US 7,710,128 B2
(45) Date of Patent: May 4, 2010

(54) METHOD AND APPARATUS FOR CONTROLLING THE SENSITIVITY AND VALUE OF A CAPACITIVE HUMIDITY SENSOR

(75) Inventors: Yousef M. Alimi, Allen, TX (US); Richard A. Davis, Plano, TX (US)

(73) Assignee: Honeywell International Inc., Morristown, NJ (US)

( * ) Notice: Subject to any disclaimer, the term of this patent is extended or adjusted under 35 U.S.C. 154(b) by 105 days.

(21) Appl. No.: 11/518,649

(22) Filed: Sep. 9, 2006

(65) Prior Publication Data

US 2008/0061802 A1 Mar. 13, 2008

(51) Int. Cl.
*G01R 27/26* (2006.01)
(52) U.S. Cl. .................... 324/689; 361/306.3; 324/664; 73/335.02
(58) Field of Classification Search .................. 324/689
See application file for complete search history.

(56) References Cited

U.S. PATENT DOCUMENTS

| | | | |
|---|---|---|---|
| 4,470,096 A | 9/1984 | Guertin | |
| 4,564,882 A | 1/1986 | Baxter et al. | 361/286 |
| 5,408,381 A | 4/1995 | Thoma et al. | 361/286 |
| 5,760,453 A * | 6/1998 | Chen | 257/529 |
| 6,222,376 B1 | 4/2001 | Tenney, III | 324/664 |
| 6,580,600 B2 | 6/2003 | Toyoda et al. | 361/523 |
| 6,690,569 B1 | 2/2004 | Mayer et al. | 361/303 |
| 6,724,612 B2 | 4/2004 | Davis et al. | 361/328 |
| 6,742,387 B2 | 6/2004 | Hamamoto et al. | 73/335.04 |
| 6,743,671 B2 * | 6/2004 | Hu et al. | 438/253 |
| 6,867,602 B2 | 3/2005 | Davis et al. | 324/664 |
| 2002/0141136 A1* | 10/2002 | Toyoda et al. | 361/302 |
| 2003/0002238 A1 | 1/2003 | Toyoda | |
| 2003/0010119 A1* | 1/2003 | Toyoda | 73/335.04 |
| 2004/0008041 A1* | 1/2004 | Davis et al. | 324/664 |
| 2004/0008471 A1* | 1/2004 | Davis et al. | 361/306.3 |
| 2004/0155751 A1* | 8/2004 | Benzel et al. | 338/35 |
| 2004/0177685 A1* | 9/2004 | Yokura et al. | 73/335.04 |
| 2004/0266159 A1* | 12/2004 | Gardecki et al. | 438/613 |

* cited by examiner

*Primary Examiner*—Timothy J Dole
*Assistant Examiner*—Benjamin M Baldridge
(74) *Attorney, Agent, or Firm*—Shumaker Sieffert, P.A.

(57) ABSTRACT

A humidity sensor apparatus and method of forming the same. A substrate can be provided upon which a plurality of humidity sensing components are disposed to form a humidity sensor thereof. Each humidity sensing component generally includes an associated particular parasitic capacitance. This parasitic capacitance is utilized to reduce and/or control a sensitivity and a total capacitance value associated with the humidity sensor without increasing a size of the humidity sensor and/or humidity sensor components (e.g., capacitors).

12 Claims, 5 Drawing Sheets

METHOD AND APPARATUS FOR CONTROLLING THE SENSITIVITY AND VALUE OF A CAPACITIVE HUMIDITY SENSOR

TECHNICAL FIELD

Embodiments are generally related to humidity sensors and method of forming the same. Embodiments are also related to capacitive-based humidity sensors. Embodiments are additionally related to techniques for controlling capacitive-based humidity sensors.

BACKGROUND

Humidity can be measured by a number of techniques. In a semiconductor-based system, humidity can be measured based upon the reversible water absorption characteristics of polymeric materials. The absorption of water into a sensor structure causes a number of physical changes in the active polymer. These physical changes can be transduced into electrical signals which are related to the water concentration in the polymer and which in turn are related to the relative humidity in the air surrounding the polymer.

Two of the most common physical changes are the change in resistance and the change in dielectric constant, which can be respectively translated into a resistance change and a capacitance change. It has been found, however, that elements utilized as resistive components suffer from the disadvantage that there is an inherent dissipation effect caused by the dissipation of heat due to the current flow in the elements necessary to make a resistance measurement. The result is erroneous readings, among other problems.

Elements constructed to approximate a pure capacitance avoid the disadvantages of the resistive elements. It is important in the construction of capacitive elements, however, to avoid the problems that can arise with certain constructions for such elements. In addition, there can also be inaccuracy incurred at high relative humidity values where high water content causes problems due to excessive stress and the resulting mechanical shifts in the components of the element. By making the component parts of the element thin, it has been found that the above-mentioned problems can be avoided and the capacitance type element can provide a fast, precise measurement of the relative humidity content over an extreme range of humidity as well as over an extreme range of temperature and pressure and other environmental variables.

Humidity sensing elements of the capacitance sensing type usually include a moisture-insensitive, non-conducting structure with appropriate electrode elements mounted or deposited on the structure along with a layer or coating of dielectric, highly moisture-sensitive material overlaying the electrodes and positioned so as to be capable of absorbing water from the surrounding atmosphere and reaching equilibrium in a short period of time. Capacitive humidity sensors are typically made by depositing several layers of material on a substrate material.

One of the challenges in designing and implementing capacitive-based humidity sensors is the difficulty faced in reducing and controlling the sensitivity of such sensors to a desired value without additional parasitic capacitance that can increase the total size of capacitor utilized. A need thus exists for an improved method and system, which can reduce and/or control the sensitivity of the sensing capacitor utilized in a capacitive-based humidity sensor.

BRIEF SUMMARY

The following summary is provided to facilitate an understanding of some of the innovative features unique to the embodiments and is not intended to be a full description. A full appreciation of the various aspects of the embodiments disclosed can be gained by taking the entire specification, claims, drawings, and abstract as a whole.

It is, therefore, one aspect of the present invention to provide for an improved humidity sensor apparatus and method of forming the same.

It is yet another aspect of the present invention to provide for an improved capacitive-based humidity sensor.

It is an additional aspect of the present invention to provide for techniques, devices and components for controlling and/or reducing the sensitivity of capacitive-based humidity sensors.

The aforementioned aspects of the invention and other objectives and advantages can now be achieved as described herein. A humidity sensor method and apparatus are disclosed. In general, a substrate can be provided, upon which a plurality of humidity sensing components are disposed to form a humidity sensor thereof. Each humidity sensing component generally includes an associated particular parasitic capacitance. This parasitic capacitance is utilized to reduce and/or control the sensitivity and total capacitance value associated with the humidity sensor without increasing the size of the humidity sensor and/or humidity sensor components (e.g., capacitors).

The substrate can be formed from silicon. A silicon dioxide layer can be configured above the silicon substrate. Additionally, a TiW layer can be formed above the silicon dioxide layer, wherein moisture-insensitive components form a connection between the silicon substrate and the TiW layer. One or more gold layers can also be located and formed above the substrate, wherein other moisture-insensitive components form a connection between the silicon substrate and the gold layer. One or more layer of humidity-sensitive polymer layer can also be formed on the TiW layer. Additionally, a layer of porous platinum can be configured above the sensitive polymer layer wherein humidity sensitive components form a connection between the porous platinum layer and the TiW layer. One or more passivation layers can also be deposited and configured above the porous platinum layer and humidity-sensitive polymer layer.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the principles of the disclosed embodiments.

DETAILED DESCRIPTION

The particular values and configurations discussed in these non-limiting examples can be varied and are cited merely to illustrate at least one embodiment and are not intended to limit the scope of the invention.

Figure 1:
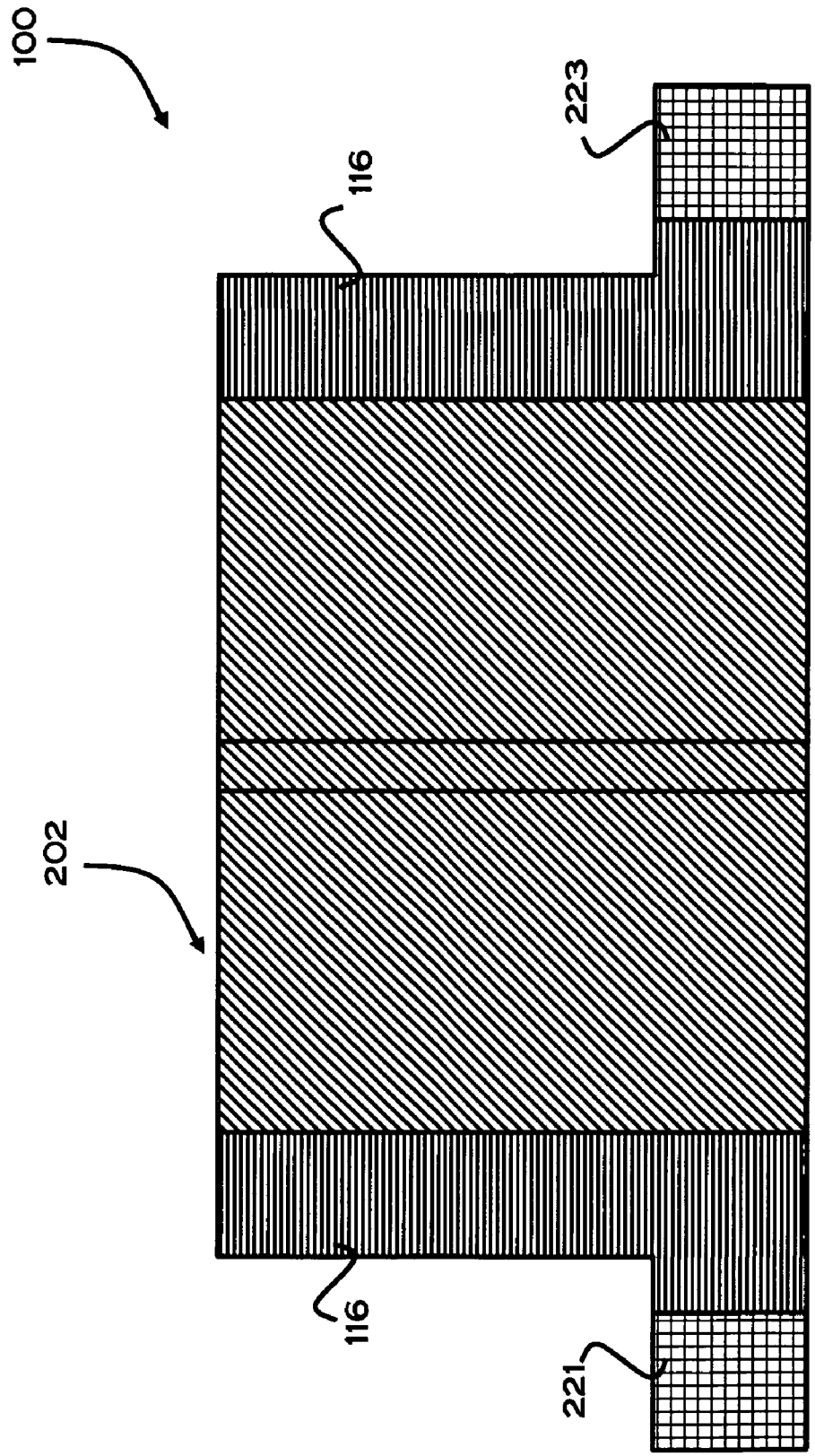
FIG. 1 illustrates a top view of a humidity sensor apparatus, which can be implemented in accordance with a preferred embodiment.
Figure 2:
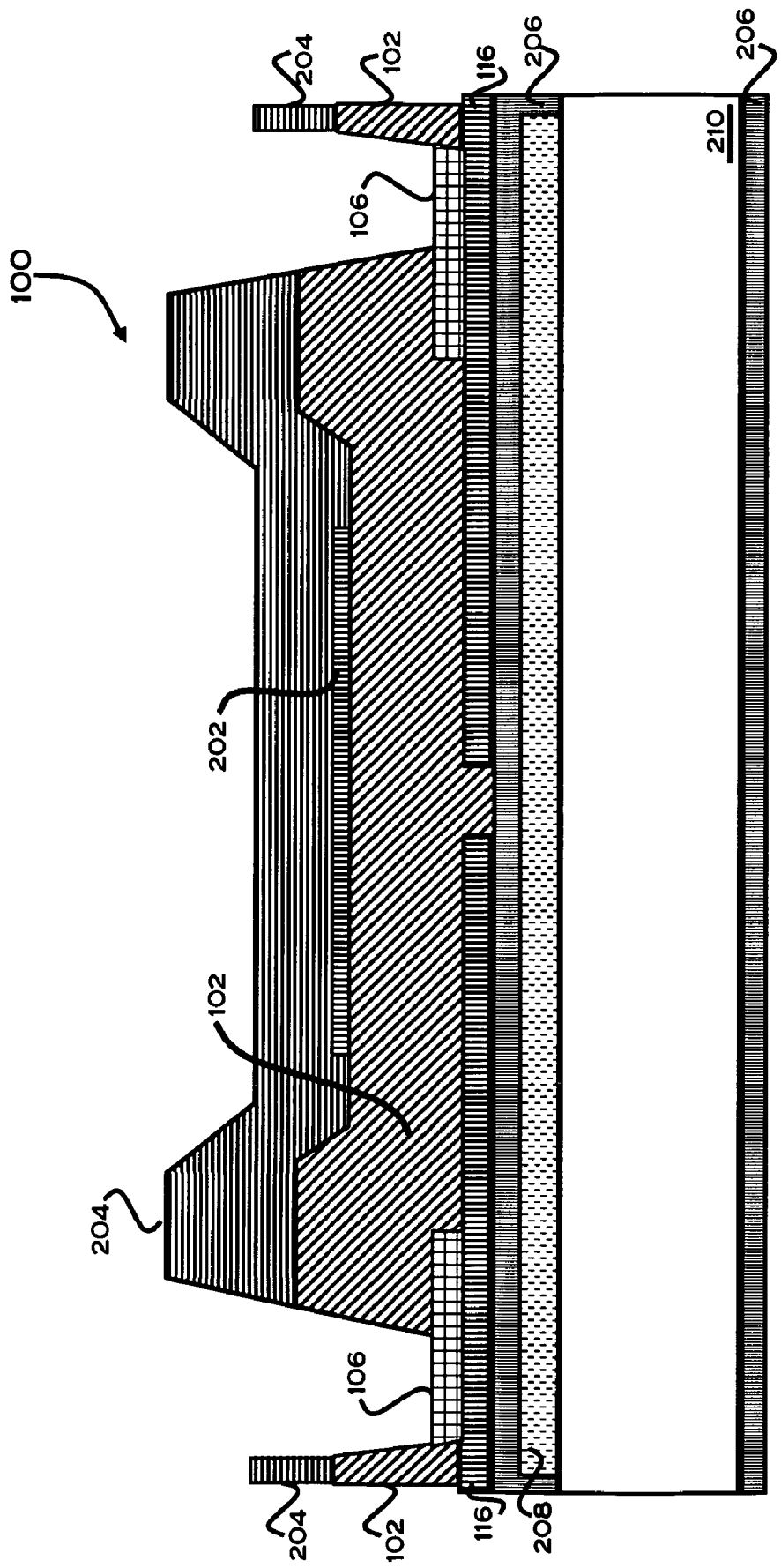
FIG. 2 illustrates a side cross-sectional view of the humidity sensor apparatus disclosed in FIG. 1.
Figure 3:
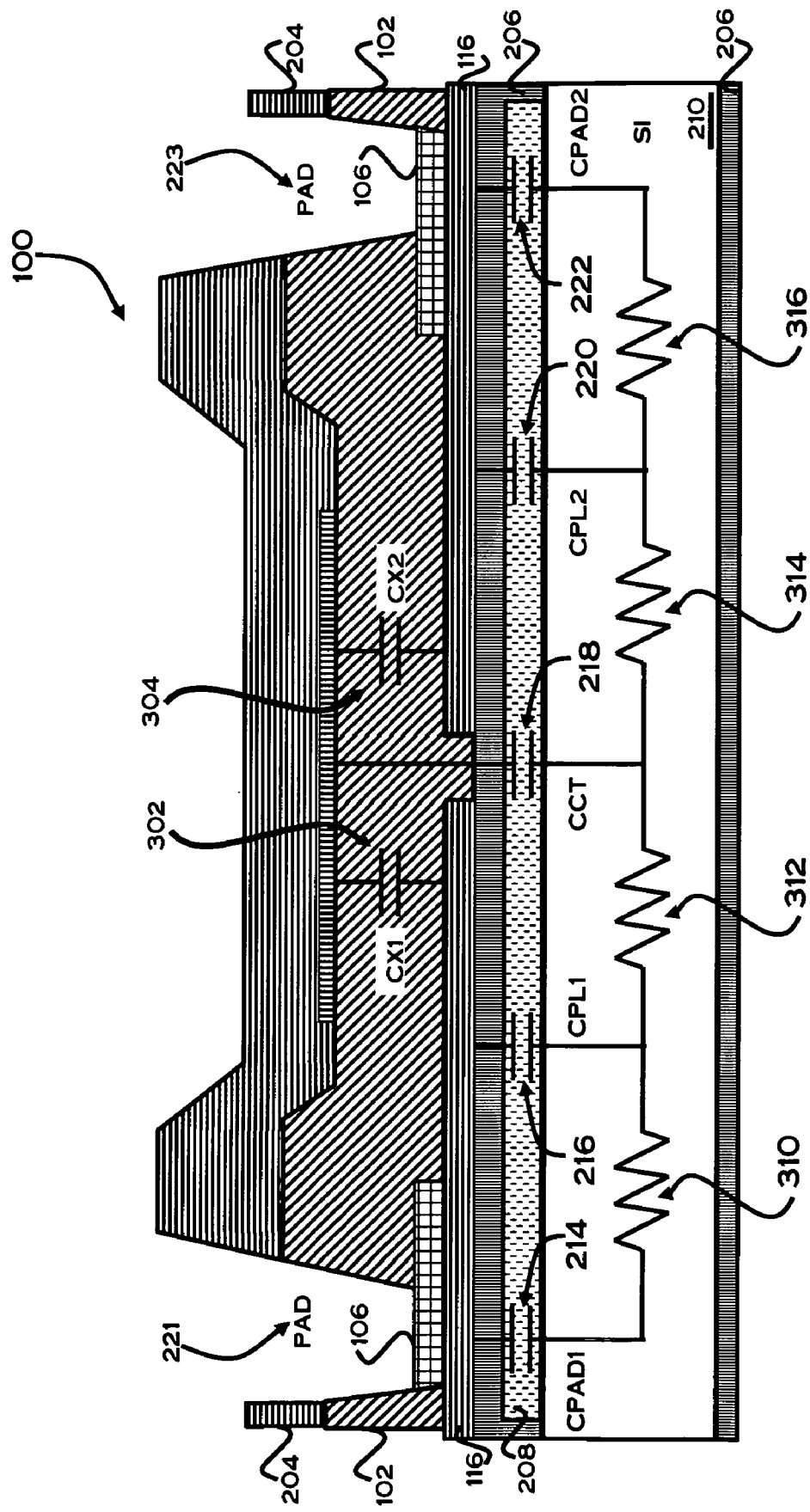
FIG. 3 illustrates a side cross-sectional view with illustration of components of the humidity sensor apparatus disclosed in FIG. 1-2.

FIG. 1 illustrates a top view of a humidity sensor apparatus 100, which can be implemented in accordance with a preferred embodiment. FIG. 2 illustrates a side cross-sectional view of the humidity sensor apparatus 100 disclosed in FIG. 1. FIG. 3 illustrates a side cross-sectional view of the humidity sensor apparatus 100 with illustration of the component formed. Note that in FIGS. 1-3, identical or similar parts or elements are generally indicated by identical reference numerals. The apparatus 100 generally includes a substrate 210, which can be formed as, for example, a silicon substrate. A silicon dioxide layer 208 can be configured above the substrate 210. A nitride layer 206 is generally located above the silicon dioxide layer 208, and above substrate layer 210.

A TiW layer 116 can be formed above the nitride layer 206 and hence, above the substrate 210. A humidity sensing medium 102, such as a polymer is configured above the TiW layer 116 and the nitride layer 206. Additionally, a porous platinum (Pt) layer 202 can also be formed above the sensing medium 102. A layer 106 of gold can also be formed above TiW layer 116 and nitride layer 206. A protective but also porous passivation layer 204 can be located above the substrate 210 and configured over the porous platinum (Pt) layer 202, and humidity sensing medium 102.

The Active Sensor Components CX1 302 and CX2 304 include the lower TiW layer 116 and upper porous platinum (Pt) layer 202 electrically conductive plates sandwiching a humidity sensing medium 102, such as a polymer. The polymer material is sensitive to humidity, and its electrically conductive property (resistance and/or capacitance) changes as it absorbs moister or as it dries.

A plurality of parasitic components 214, 216, 218, 220 and 222 are also provided and formed on the substrate 210. Such non-humidity sensing components 214, 216, 218, 220 and 222 are provided as controlling capacitors and connect the TiW layer 116 with the substrate 210. Pad areas 221 and 223 are also formed through the arrangements of the TiW layer 116, and the layer 106 of gold. A plurality of resistive components 310, 312, 314, and 316 are also provided at the substrate layer 210.

By implementing the configuration of apparatus 100 depicted in FIGS. 1-3, the sensitivity of the apparatus 100 can be reduced and/or controlled to a desired value without an additional parasitic capacitance that otherwise would increase the size of the total capacitance value associated with the humidity sensing components 302, and 304.

Figure 4:
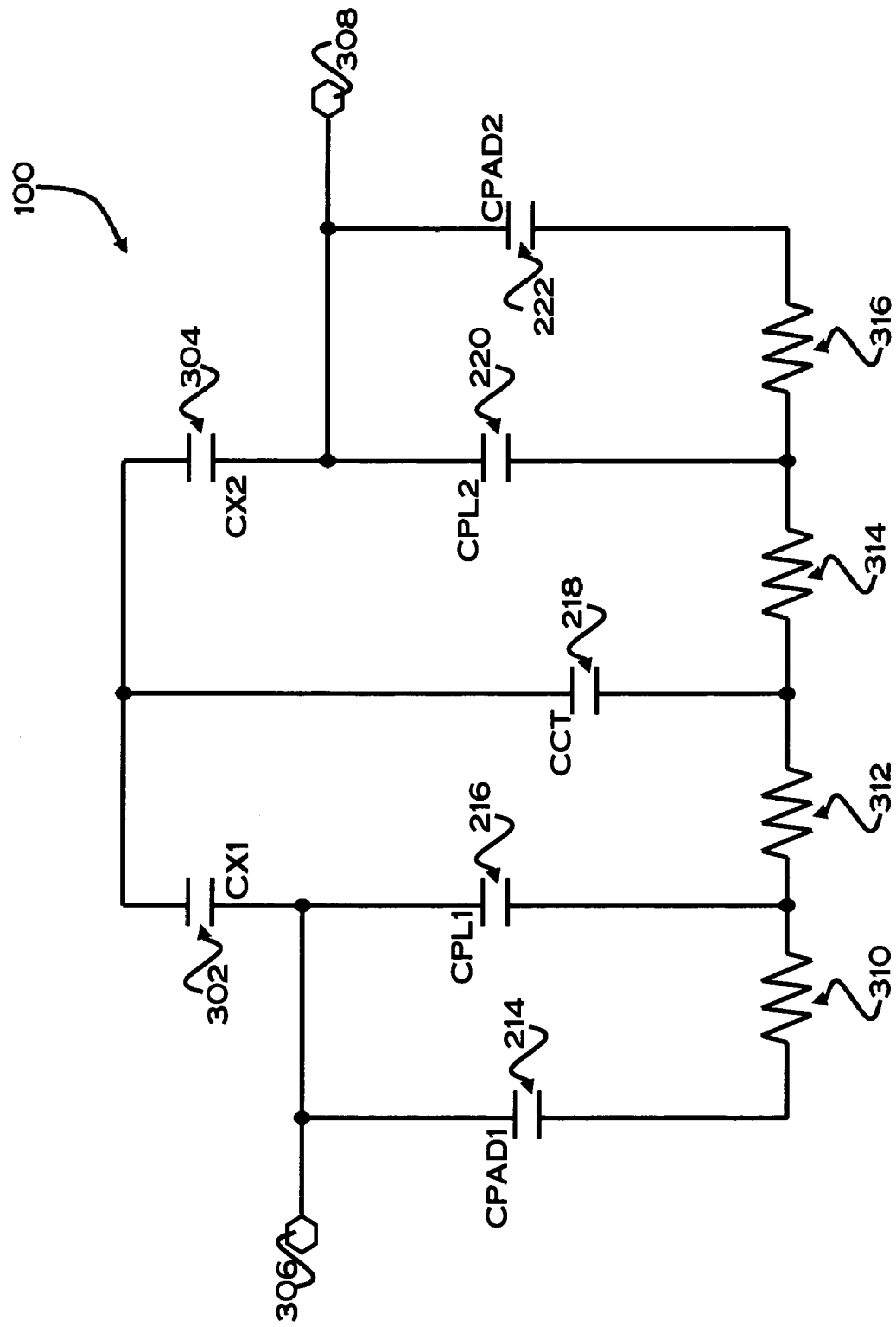
FIG. 4 illustrates a schematic diagram of the humidity sensor apparatus disclosed in FIGS. 1-3 in accordance with a preferred embodiment.

FIG. 4 illustrates an electrical schematic diagram of a humidity sensor apparatus 100 disclosed in FIGS. 1-3 in accordance with a preferred embodiment. Note that in FIGS. 1-3 and 4, identical or similar parts or elements are generally indicated by identical reference numerals. As indicated in the schematic diagram depicted in FIG. 4, the capacitor 214 is generally connected to a resistor 310, which in turn is connected electrically to a resistor 312 and the capacitor 216. The resistor 312 is electrically connected to capacitor 218 and to a resistor 314. The capacitor 214 is also connected electrically to a node 306 and to an active humidity capacitor 302. An active humidity capacitor 304 is connected electrically to the active humidity capacitor 302 and to the capacitor 218.

The capacitor 220 is electrically connected to the active humidity capacitor 304 and to resistors 314 and 316. The capacitor 222 is connected electrically between the resistor 316 and a node 308. The capacitor 222 is electrically connected to the capacitor 220 and the active humidity capacitor 304 at node 308. The arrangement depicted in the schematic diagram of apparatus 100 indicated in FIG. 4 takes advantage of existing parasitic capacitances 214, 216, 218, 220, and 222 created by the active humidity capacitor plates of capacitors 302, and 304 to control the sensitivity and thus the total value of the capacitance associated with the humidity sensor apparatus 100.

Figure 5:
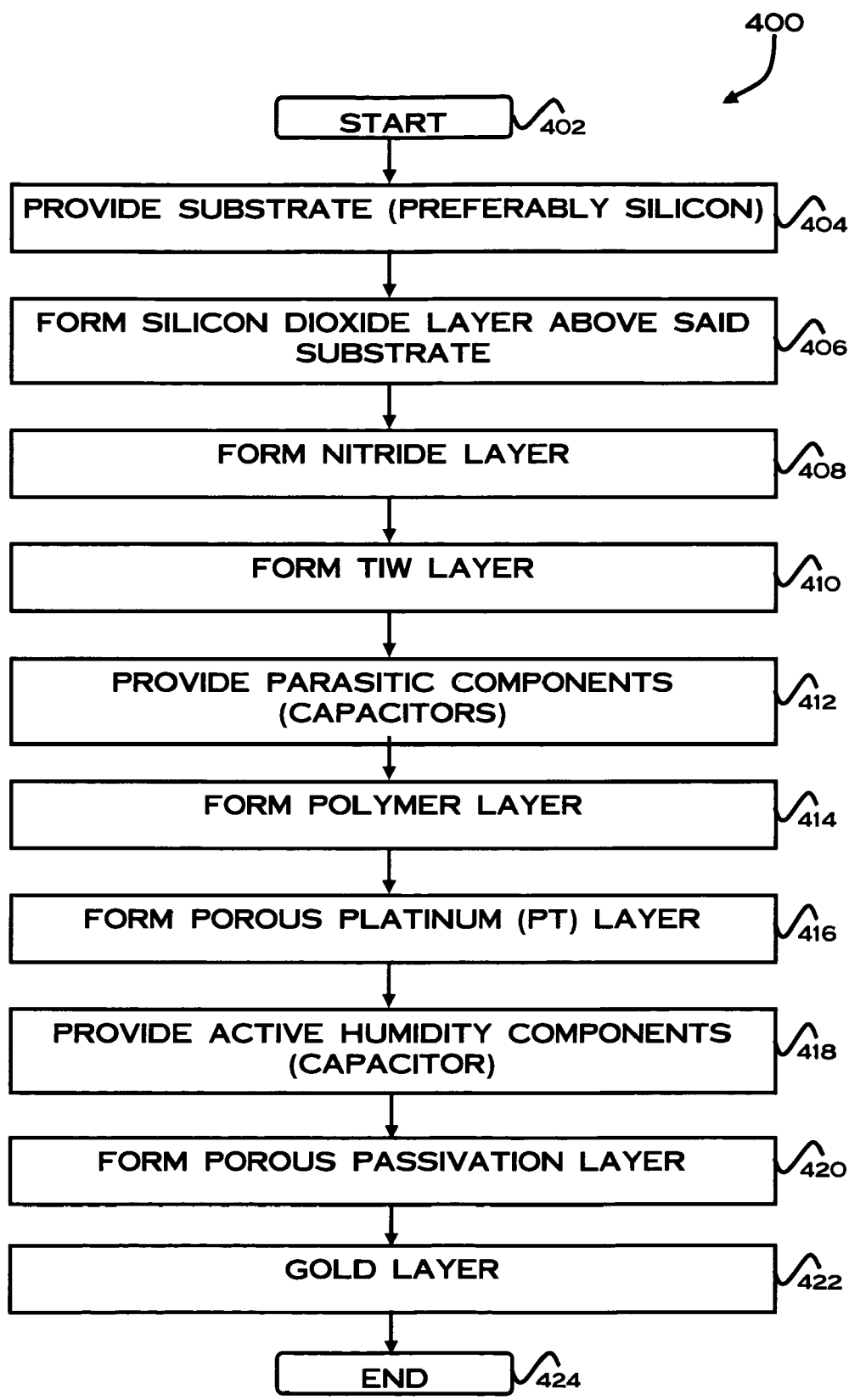
FIG. 5 illustrates a high-level flow chart of operations depicted logical operational steps that can be implemented for forming the apparatus depicted in FIGS. 1-4, in accordance with an alternative embodiment.

FIG. 5 illustrates a high-level flow chart of operations depicting logical operational steps of a method 400 that can be implemented for forming the apparatus 100 depicted in FIGS. 1-4, in accordance with an alternative embodiment. In general, the process begins as indicated at block 402. As indicated at block 404, the silicon substrate 210 can be provided. Next, as indicated in 406, the silicon dioxide layer 208 can be formed above the substrate 210. Thereafter, as depicted at block 408, the nitride layer 206 can be formed above the silicon dioxide layer 208.

Next, as described at block 410, the TiW layer 116 can be configured above the substrate 210 and silicon dioxide layer 208, and the nitride layer 206. Thereafter, the parasitic components (capacitors) 214, 216, 220, 222 can be provided as described at block 412. Next, as depicted at block 414, the layer of polymer can be formed above the TiW layer 116. Next, as indicated at block 416, a porous platinum (Pt) layer 202 can be configured above the polymer layer 102 Therefore, the sensitive components (capacitor) 302, 304, and parasitic component (capacitor) 218 can be provided as described at block 418. Following processing of the operation depicted at block 416, the operation indicated at block 420 can be processed in which the passivation layer 204 is configured above the porous platinum (Pt) layer 202, and the Polymer layer 102. Finally, as indicated at block 422, the gold layer 106 can be formed. The process can then terminate, as indicated at block 424.

Note that although a particular number and order of steps are depicted in method 400 of FIG. 5, it can be appreciated that in accordance with alternative embodiments, certain steps can be formed prior to or after other operational steps, depending upon design considerations.

It is also important to note that the Combination of Oxide and Nitride to form the parasitic capacitance can be selected to adjust versatility of parasitic capacitances. Also, in order to reduce the drift due to a prolonged exposure to high levels of humidity, nitride can be used to seal the oxide as shown in FIGS. 2 and 3, because oxide is much more sensitive to moisture at higher levels of humidity, while nitride is not.

It will be appreciated that variations of the above-disclosed and other features and functions, or alternatives thereof, may be desirably combined into many other different systems or applications. Also various presently unforeseen or unanticipated alternatives, modifications, variations or improvements therein may be subsequently made by those skilled in the art which are also intended to be encompassed by the following claims.

What is claimed is:

1. A method for forming a capacitive humidity sensor, comprising:
   providing a substrate;
   depositing a first dielectric layer on said substrate;
   depositing a second dielectric layer on said first dielectric layer; and
   forming a first and a second series connected active humidity capacitor stacked on said second dielectric layer, said first and said second active humidity capacitors comprising:

a first bottom and a second bottom sensing capacitor electrode separated from one another by a gap, a humidity sensing medium on said first and second bottom sensing capacitor electrodes, a top sensing capacitor electrode on said humidity sensing medium positioned over said first bottom and second bottom sensing capacitor electrodes, wherein said top sensing capacitor electrode comprises a porous layer for allowing humidity to reach said humidity sensing medium, and a first bond pad coupled to said first bottom sensing capacitor electrode and a second bond pad coupled to said second bottom sensing capacitor electrode;

wherein a first and a second series connected parasitic capacitor stacked below said first and said second series connected active humidity capacitor is provided comprising (i) top plates comprising said first bottom and said second bottom sensing capacitor electrodes, (ii) a dielectric comprising said second dielectric layer on said first dielectric layer, and (iii) bottom plates comprising said substrate, and wherein said first and second parasitic capacitors control a total capacitance of said capacitive humidity sensor to obtain a desired value for sensitivity of said capacitive humidity sensor without increasing its size.

2. The method of claim 1 wherein said second dielectric layer seals said first dielectric layer from moisture including sealing sidewalls of said first dielectric layer, said second dielectric layer being less moisture permeable as compared to said first dielectric layer, and wherein said sealing sidewalls of said first dielectric layer associated with said parasitic capacitors blocks moisture reaching said first dielectric layer to reduce a drift in said capacitive humidity sensor due to exposure to humidity.

3. The method of claim 1 wherein said first dielectric layer comprises a silicon dioxide layer, wherein said-second dielectric layer comprises a nitride layer and wherein said first bottom and said second bottom sensing capacitor electrodes comprise TiW layer.

4. The method of claim 3 wherein said humidity sensing medium comprises at least one humidity-sensitive polymer layer.

5. The method of claim 4 wherein said top sensing capacitor electrode comprises at least one porous platinum layer.

6. The method of claim 1 wherein said first and said second bond pad comprise gold.

7. A humidity sensor apparatus, comprising:

a substrate;

a first dielectric layer on said substrate;

a second dielectric layer on said first dielectric layer; and a first and a second series connected active humidity capacitor stacked on said second dielectric layer, said first and said second active humidity capacitors comprising:

a first bottom and a second bottom sensing capacitor electrode separated by a gap, a humidity sensing medium on said first bottom and second bottom sensing capacitor electrodes, a top sensing capacitor electrode on said humidity sensing medium positioned over said first bottom and second bottom sensing capacitor electrodes, wherein said top sensing capacitor electrode comprises a porous layer for allowing humidity to reach said humidity sensing medium; and a first bond pad coupled to said first bottom sensing capacitor electrode and a second bond pad coupled to said second bottom sensing capacitor electrode wherein a first and a second series connected parasitic capacitor stacked below said first and said second series connected active humidity capacitor is provided comprising (i) top plates comprising said first bottom and said second bottom sensing capacitor electrodes, (ii) a dielectric comprising said second dielectric layer on said first dielectric layer, and (iii) bottom plates comprising said substrate, and wherein said first and second parasitic capacitors control a total capacitance of said capacitive humidity sensor to obtain a desired value for sensitivity of said capacitive humidity sensor without increasing its size.

8. The apparatus of claim 7 wherein said second dielectric layer seals said first dielectric layer from moisture including sealing sidewalls of said first dielectric layer, said second dielectric layer being less moisture permeable as compared to said first dielectric layer and wherein said sealing sidewalls of said first dielectric layer associated with said parasitic capacitors blocks moisture reaching said first dielectric layer to reduce a drift in said capacitive humidity sensor due to exposure to humidity.

9. The apparatus of claim 7 wherein said first dielectric layer comprises a silicon dioxide layer, wherein said second dielectric layer comprises a nitride layer and wherein said first bottom and said second bottom sensing capacitor electrodes comprise a TiW layer.

10. The apparatus of claim 9 wherein said first and said second bond pads comprise gold.

11. The apparatus of claim 7 wherein said humidity sensing medium comprises a humidity-sensitive polymer layer.

12. The apparatus of claim 7 wherein said top sensing capacitor electrode comprises at least one porous platinum layer.

* * * * *